US012714184B1

(12) United States Patent
Steller

(10) Patent No.: US 12,714,184 B1
(45) Date of Patent: Aug. 25, 2026

(54) SLIP-ON ORTHOTIC FOOT SUPPORT FOR ARCH AND BALL OF FOOT

(71) Applicant: Stephen Steller, Clearwater, FL (US)

(72) Inventor: Stephen Steller, Clearwater, FL (US)

(73) Assignee: Endless Sandal LLC., Dover, DE (US)

( * ) Notice: Subject to any disclaimer, the term of this patent is extended or adjusted under 35 U.S.C. 154(b) by 1 day.

(21) Appl. No.: 17/978,625

(22) Filed: Nov. 1, 2022

Related U.S. Application Data

(60) Provisional application No. 63/274,061, filed on Nov. 1, 2021.

(51) Int. Cl.
*A43B 7/1475* (2022.01)
*A61F 5/01* (2006.01)

(52) U.S. Cl.
CPC .......... *A43B 7/1475* (2013.01); *A61F 5/0111* (2013.01)

(58) Field of Classification Search
CPC .. A43B 5/12; A43B 3/12; A43B 3/105; A43B 3/103; A43B 3/122; A43B 3/126; A43B 3/108; A43B 3/128; A43B 7/1415; A43B 7/142; A43B 7/22; A61F 5/0111; A61F 5/14; A61F 5/019; A61F 13/067
USPC .......................................................... 36/11.5
See application file for complete search history.

(56) References Cited

U.S. PATENT DOCUMENTS 1,407,992 A * 2/1922 Doody et al. .......... A43B 3/126 36/11.5
2,237,652 A * 4/1941 Capezio .................. A43B 5/12 36/94
2,812,944 A 11/1957 Finch
2,947,095 A * 8/1960 Miyachi ................ A43B 3/106 36/94
4,272,070 A 6/1981 Schachner et al.
4,405,127 A 9/1983 Miller
4,944,478 A 7/1990 Sullivan
5,643,148 A * 7/1997 Naville ................. A63B 25/10 482/79
7,603,728 B2 10/2009 Roth
7,780,575 B1 8/2010 Goodwin, III et al.
8,047,972 B1 11/2011 Dean et al.
D650,024 S 12/2011 Ivanov
8,231,093 B2 7/2012 Tran
(Continued)

FOREIGN PATENT DOCUMENTS

WO WO2017149182 A1 8/2017

*Primary Examiner* — Grady Alexander Nunnery
(74) *Attorney, Agent, or Firm* — John Rizvi; John Rizvi, P.A.—The Patent Professor®

(57) ABSTRACT

A slip-on orthotic foot support is constructed and arranged to support the arch and the ball of a wearer's foot. The foot support may be configured as a partial sandal having neither under-toe nor under-heel portions, and comprises a sole defining a mid-foot support affixed to an upper transverse strap, and a retention wedge or toe strap affixed to and extending vertically between the sole and the upper transverse strap. The foot support may additionally include an arch support and a ball-of-foot pad on an upper surface of the sole. The foot support provides hands-free, slip-on and slip-off orthotic "stand-alone" footwear that is not meant to be worn with shoes. The foot support may be beneficially used by the wearer to wear instead of shoes or going barefoot around the house. The foot support may be made of waterproof materials and may include an anti-slip bottom.

10 Claims, 5 Drawing Sheets

(56) References Cited

U.S. PATENT DOCUMENTS

| | | | | |
|---|---|---|---|---|
| 8,690,742 | B1 | 4/2014 | Herman et al. | |
| 9,050,493 | B2 | 6/2015 | Perez | |
| 9,427,612 | B1 | 8/2016 | Swanson | |
| 9,738,233 | B1 | 8/2017 | Schwefel | |
| 2006/0249638 | A1 | 11/2006 | Ehrke | |
| 2008/0179905 | A1 | 7/2008 | Park | |
| 2008/0196269 | A1* | 8/2008 | Bathum | A43B 3/108 36/43 |
| 2008/0307677 | A1* | 12/2008 | Nguyen | A61F 5/14 36/155 |
| 2010/0048368 | A1 | 2/2010 | Donofrio | |
| 2010/0269371 | A1* | 10/2010 | Gray | A43B 7/141 36/43 |
| 2012/0116326 | A1* | 5/2012 | Candella | A43B 3/128 604/293 |
| 2012/0129658 | A1 | 5/2012 | Hunt et al. | |
| 2013/0052622 | A1 | 2/2013 | Calabrese | |
| 2014/0202030 | A1* | 7/2014 | Cheng | A43B 3/105 36/11.5 |
| 2015/0243185 | A1 | 8/2015 | Purdy | |
| 2019/0046835 | A1 | 2/2019 | Henninger et al. | |
| 2020/0009413 | A1 | 1/2020 | Berklund et al. | |
| 2020/0139182 | A1 | 5/2020 | Price | |

* cited by examiner

SLIP-ON ORTHOTIC FOOT SUPPORT FOR ARCH AND BALL OF FOOT

CROSS-REFERENCE TO RELATED APPLICATIONS

This application claims the benefit of U.S. Provisional Patent Application No. 63/274,061, filed on Nov. 1, 2021, which is incorporated by reference herein in its entirety.

FIELD OF THE INVENTION

The present invention relates generally to orthotic devices, and more particularly, to a slip-on orthotic foot support sandal.

BACKGROUND OF THE INVENTION

While many orthotic devices exist, an unresolved need exists for a slip-on orthotic foot support for supporting a foot arch and a ball of a foot of a wearer without the wearer having to wear a shoe.

Arch supports have been developed which support the metatarsals. Such arch supports may individually support and elevate either of the five metatarsals of the foot or may be located under-any part of the foot to elevate and hold any one of the metatarsal in its natural position. Arch supports may be held in place by a flexible band and have an insertable pad held in place within a pocket thereof, by the band.

Supports are known which provide support and cushioning to the foot to alleviate plantar fasciitis, fallen arches, heel pain, bunions, and other conditions. Plantar fasciitis arch support (PFAS) devices may include splints or blocks held on the foot by a flexible band to provide an "ergonomic compression device" that administers a measured pressure along the tissue on the plantar surface of the foot for purpose of relieving the pain and inflammation of plantar fasciitis. Such devices may work by directly compressing and stretching the plantar fascia in order to relieve pressure at the plantar fascia attachment points. Such devices are either medical splints not meant to be walked on, or are devices which provide arch supports that are not meant to be worn without a shoe. None of these devices are meant for use to walk without a shoe.

Use of these devices while walking may be uncomfortable or unsafe. Use of these devices while walking may cause foot injury. Further, use of these devices while walking may even cause injury if the wearer slips and falls because these devices are not configured to be worn while walking.

Orthotic shoes or inserts may include portions meant only to be incorporated into a shoe or worn in a shoe. Such orthotic shoes or inserts may offer additional support for; a) the three arches of the foot; b) a heel cradle that aligns the calcareous and therefore provides the user with proper gait; or c) a ridge to provide traction for the metatarsophalangeal joints. Teachings in the field reflect the medical benefit of all such orthotic soles is diminished when the footwear fits incorrectly, as is most commonly seen with open or loose footwear such as sandals, clogs and thongs. Strap fixation of the shoe or orthotic is taught as a requirement to ensure the foot is positioned appropriately across the three arches of the foot thus achieving the intended medical and comfort benefit of additional support to the calcareous and the metatarsophalangeal joints. Such orthotic shoes and inserts are not meant to be used without a shoe, and are taught to be required to include straps.

Accordingly, a need exists for a solution to one or more of the aforementioned problems. A need exists for a hands-free slip-on, and hands free slip-off orthotic that supports the middle of the foot between the distal end of the heel and the distal end of the metatarsal bones. A need exists for an orthotic that is designed to support the bottom of the mid foot, which provides no support, padding or sole under the heel or toes and is not meant to be worn with shoes. A need exists for a slip-on slip-off orthotic that has no under-toe portion and no under-heel portion. A further need exists for such an orthotic that provides a mid-foot support including an arch support and a ball of foot pad. A need exists for a hands-free slip-on slip-off orthotic to wear around the home instead of conventional shoes or conventional sandals. A need exists for an orthotic to provide the wearer the feeling of walking around barefoot while still having support under the middle soft spot of the foot. A need exists for a slip-on slip-off orthotic sandal that may be worn by individuals that have fallen arches, thinning of the ball of the foot, or other foot problems. A need exists for such a slip-on slip-off orthotic that may be water resistant and include an anti-slip bottom and may be worn in the shower to provide the wearer continued support while standing in the shower.

SUMMARY OF THE INVENTION

The present invention is directed to a slip-on orthotic foot support constructed and arranged to support the arch and the ball of a wearer's foot. The foot support may be configured as a partial sandal having neither under-toe nor under-heel portions, and comprises a mid-foot support and an upper transverse strap affixed at lateral and medial portions thereof, and a retention wedge or toe strap affixed to and extending between the mid-foot support and the upper transverse strap. The foot support may additionally include an arch support and a ball-of-foot pad on an upper surface of the mid-foot support. The foot support provides hands-free, slip-on and slip-off orthotic "standalone" footwear that is not meant to be worn with shoes. The foot support may be beneficially used by the wearer instead of wearing shoes or conventional sandals, and instead of going barefoot around the house. The foot support may be made of waterproof materials and may include an anti-slip bottom.

In a first implementation of the invention, a slip-on orthotic foot support for supporting a foot arch and a ball of a foot of a wearer without the wearer having to wear a shoe, has a top, a bottom, a front, a rear, a medial side. The slip-on orthotic foot support may comprise a sole connected to an upper transverse strap, and a toe strap connected to the sole and the upper transverse strap and extending vertically therebetween.

In one aspect, the sole may comprise a sole top surface, a sole bottom surface, a lower toe strap slit, a medial sole area and a lateral sole area. The sole may define a mid-foot support.

In another aspect, the upper transverse strap has an upper transverse strap top surface, an upper transverse strap bottom surface, an upper transverse strap medial end, an upper transverse strap medial end distal flap, an upper transverse strap lateral end, an upper transverse strap lateral end distal flap, and an upper toe strap slit.

In a further aspect, the toe strap comprises a toe strap first upper end, a toe strap first upper flap, a toe strap second upper end, a toe strap second upper flap, a toe strap intermediate portion, a toe strap first lower end, a toe strap first lower flap, a toe strap second lower end, and a toe strap second lower flap.

In one aspect, the slip-on orthotic foot support may comprise an arch support fixed to the mid-foot support, the arch support located proximal to the medial side of the slip-on orthotic foot support. The slip-on orthotic foot support may further comprise a ball of foot pad fixed to the mid-foot support proximal to a central area of the mid-foot support.

In one aspect, the upper transverse strap is attached to the sole by fixation of the upper transverse strap medial end distal flap to the sole bottom surface at the medial sole area, and fixation of the upper transverse strap lateral end distal flap to the sole bottom surface at the lateral sole area.

In another aspect, the intermediate portion of the toe strap extends vertically between the sole and the upper transverse strap, the toe strap first lower flap and the toe strap second lower flap extend downwardly through the lower toe strap slit, the toe strap first lower flap is attached to the sole by fixation of the toe strap first lower flap to the sole bottom surface, the toe strap second lower flap is attached to the sole by fixation of the toe strap second lower flap to the sole bottom surface, the toe strap first upper flap and the second toe strap upper flap extend through the upper to strap slit, the toe strap first upper flap is attached to the upper transverse strap by fixation of the toe strap first upper flap to the upper transverse strap top surface and the toe strap second upper flap is attached to the upper transverse strap by fixation of the toe strap second upper flap to the upper transverse strap top surface.

In a still further aspect, the wearer may easily don the slip-on orthotic foot support by slipping the foot of the wearer into the slip-on orthotic foot support to support the foot arch and the ball of the foot of the wearer without the wearer having to wear a shoe, and easily remove the slip-on orthotic foot support by slipping the foot of the wearer out of the slip-on orthotic foot support.

In another aspect, the slip-on orthotic foot support and its components may be made of waterproof materials.

In yet another aspect, the slip-on orthotic foot support may further comprise an anti-slip bottom.

In a further aspect, the slip-on orthotic foot support may further comprise an inner sole affixed to the sole top surface.

In a still further aspect, the slip-on orthotic foot support may further comprise an outer sole affixed to the sole bottom surface.

In one aspect, the slip-on orthotic foot support of the present invention provides an unprecedented solution. The hands-free slip-on, and hands free slip-off orthotic supports the middle of the foot between the distal end of the heel and the distal end of the metatarsal bones. The present invention provides an orthotic designed to support the bottom of the mid foot, which has no under-toe portion and no under-heel portion, and provides no support, padding or sole under the heel or toes. The orthotic provides a mid-foot support which may include an arch support and a ball of foot pad. The present invention provides a hands-free slip-on slip-off orthotic which is not meant to be worn with shoes, and may be worn around the home instead of conventional shoes or conventional sandals. The orthotic is constructed and arranged to provide the wearer the feeling of walking around barefoot while still having support under the middle soft spot of the foot. The orthotic may be worn by individuals that have fallen arches, thinning of the ball of the foot, or other foot problems. The orthotic may be water resistant and include an anti-slip bottom, and may be worn in a shower to provide the wearer continued support while standing in the shower.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word “exemplary” or “illustrative” means “serving as an example, instance, or illustration.” Any implementation described herein as “exemplary” or “illustrative” is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms “upper”, “lower”, “left”, “rear”, “right”, “front”, “vertical”, “horizontal”, and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 4:
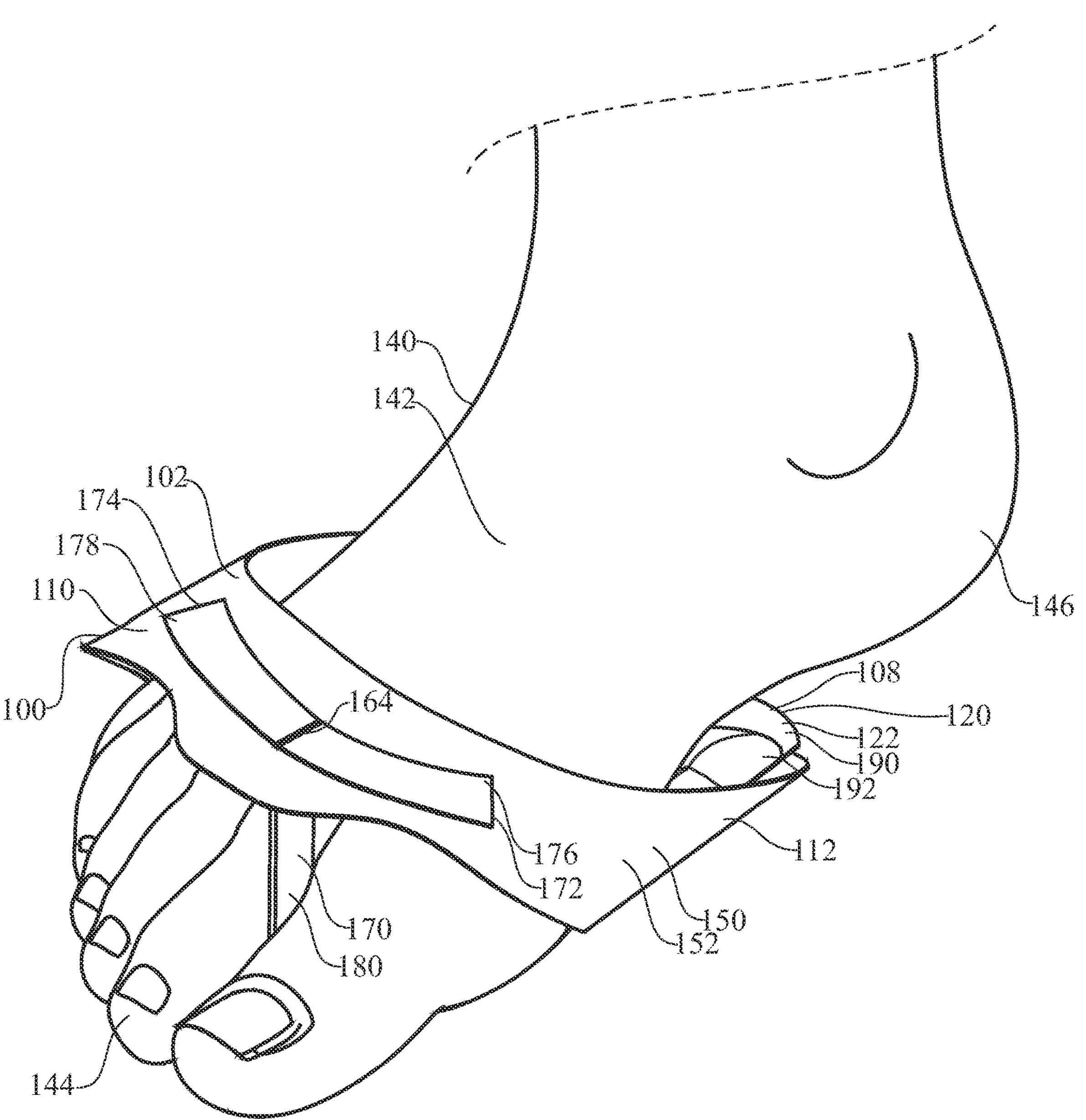
FIG. 4 presents a top, front, left perspective view of a slip-on orthotic foot support worn on the foot of a wearer, in accordance with an illustrative embodiment of the present invention.
Figure 5:
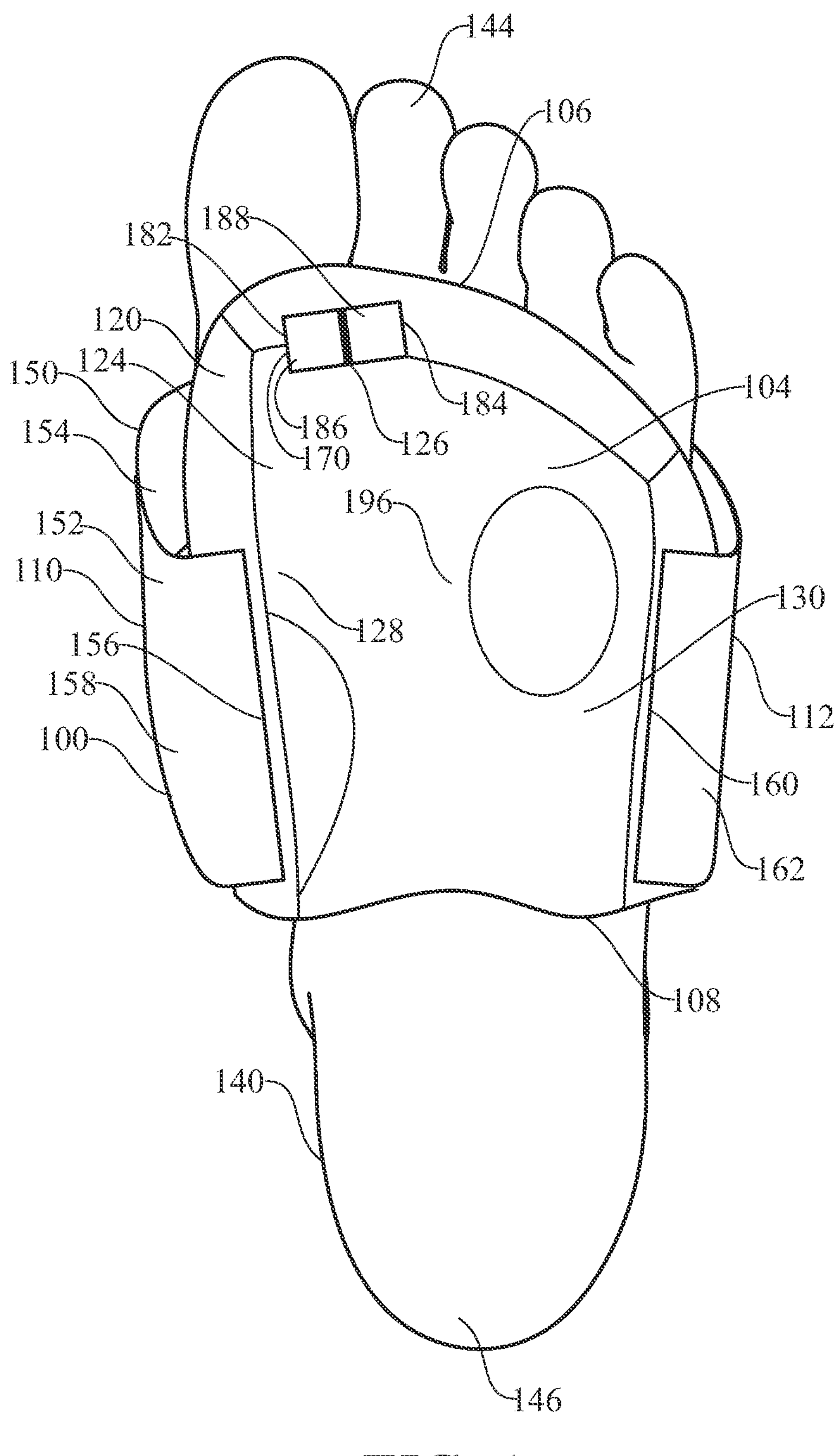
FIG. 5 presents a bottom plan view of the slip-on orthotic foot support as in FIG. 4.

Shown throughout the figures, a slip-on orthotic foot support 100 (hereinafter “foot support 100”) is shown. The foot support 100 (shown at FIGS. 1-5) may provide an “end-less sandal”, and is constructed and arranged to support the arch and the ball of a foot of a wearer 140 (as seen at FIGS. 4-5). The foot support 100 may be configured as a partial sandal having neither under-toe nor under-heel portions.

Figure 1:
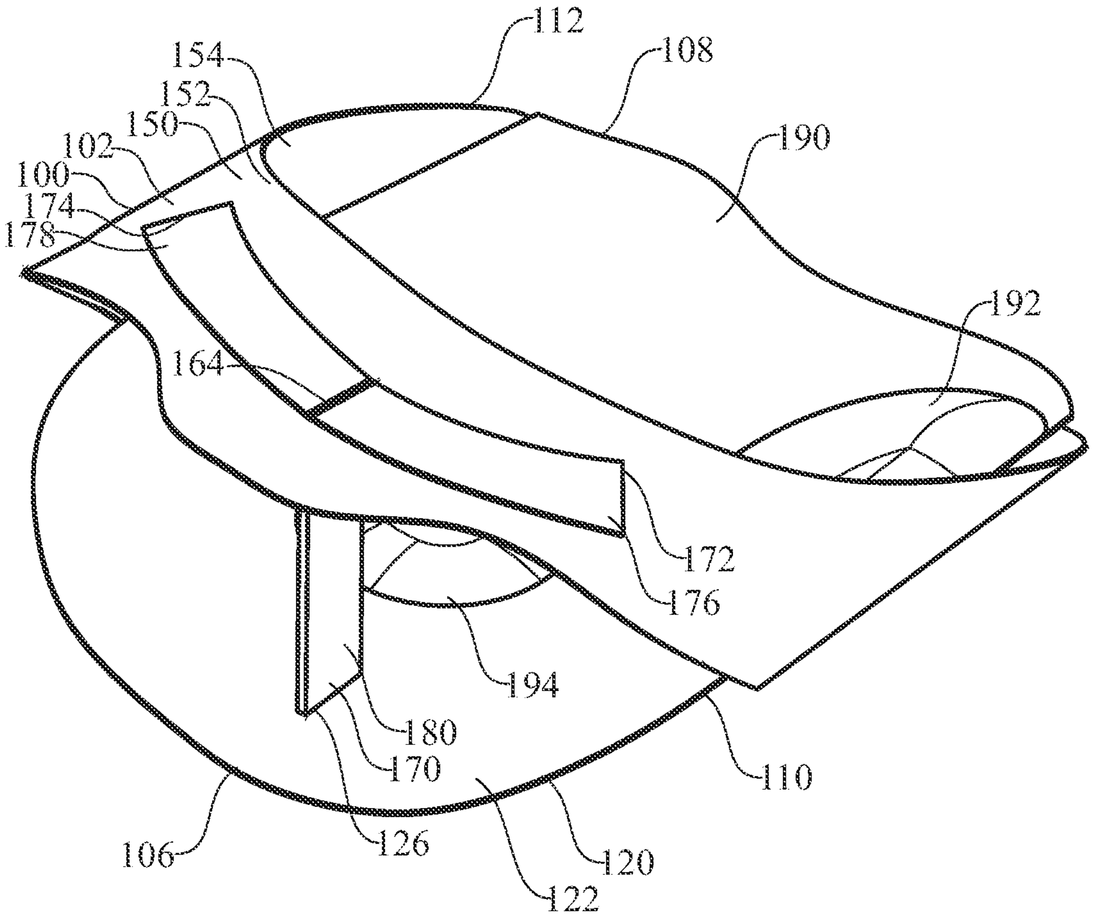
FIG. 1 presents a top, front, left perspective view of a slip-on orthotic foot support in accordance with an illustrative embodiment of the present invention.
Figure 2:
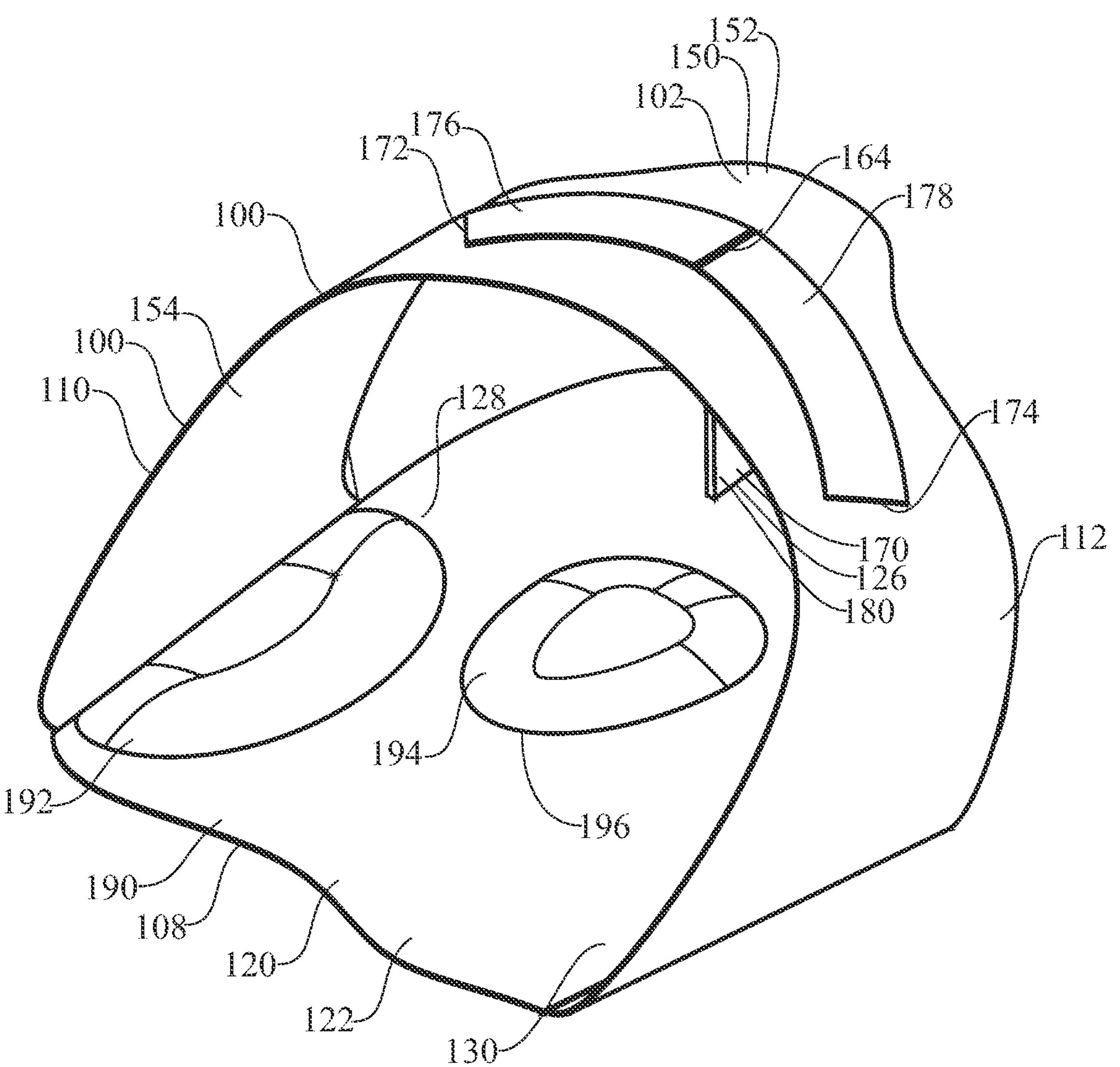
FIG. 2 presents a top, rear, right perspective view of the slip-on orthotic foot support illustrated in FIG. 1.
Figure 3:
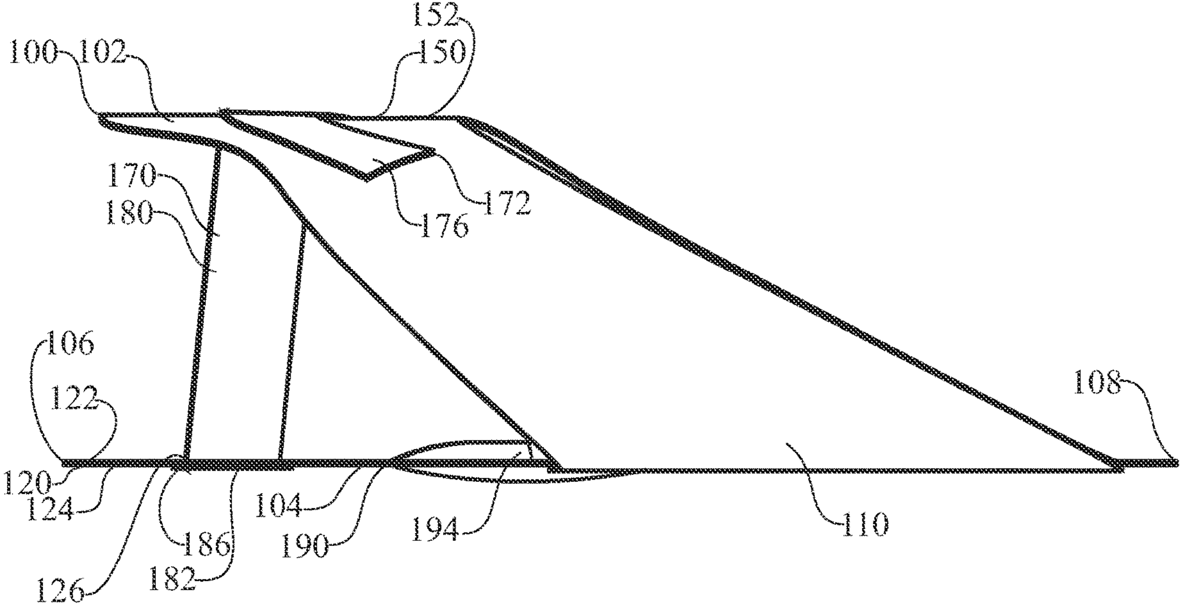
FIG. 3 presents a side view of the slip-on orthotic foot support illustrated in FIG. 1.

Referring to FIGS. 1-3, the foot support in accordance with an exemplary embodiment of the present invention is shown. FIG. 1 provides a top, front, left perspective view of the foot support 100. FIG. 2 provides a top, rear, right perspective view of the foot support 100. FIG. 3 present a side view of the foot support 100. The foot support 100 may comprise a sole 120 affixed to an upper transverse strap 150 at lateral and medial portions thereof, and a toe strap 170 (or retention wedge) affixed to and extending between the sole 120 and the upper transverse strap 150. The foot support 100 may additionally include an arch support 192 and a ball-of-foot pad 194 on the sole top surface 122.

The foot support 100 provides hands-free, slip-on and slip-off orthotic "stand-alone" footwear that is not meant to be worn with shoes. The foot support 100 may be beneficially used by the wearer to wear instead of shoes or going barefoot around the house. The foot support 100 may be made of waterproof materials and may include an anti-slip bottom.

As shown at FIGS. 4-5, the foot support 100 is shown on the foot of a wearer 140. The foot support 100 constructed and arranged to support a foot arch and a ball of a foot of a wearer 140 without the wearer having to wear a shoe.

Referring again to FIGS. 1-3 and 5, the foot support 100 has a top 102, a bottom 104 (best seen at FIG. 5), a front 106 (best seen at FIG. 1), a rear 108 (best seen at FIG. 2), a medial side 110 and a lateral side 112. The foot support may comprise a sole 120 connected to an upper transverse strap 150, and a toe strap 170 (or retention wedge) connected to the sole 120 and the upper transverse strap 150 and extending vertically therebetween (best seen at FIG. 3).

The sole 120 may comprise a sole top surface 122 (best seen at FIGS. 1-2), a sole bottom surface 124 (best seen at FIG. 5), a lower toe strap slit 126 (best seen at FIG. 5), a medial sole area 128 (best seen at FIG. 2), and a lateral sole area 130 (best seen at FIG. 2). The sole may define a mid-foot support 190.

The upper transverse strap 150 has an upper transverse strap top surface 152 and an upper transverse strap bottom surface 154. As best seen at FIG. 5, the upper transverse strap 150 has an upper transverse strap medial end 156, an upper transverse strap medial end distal flap 158, an upper transverse strap lateral end 160, and an upper transverse strap lateral end distal flap 162. The upper transverse strap 150 further comprises an upper toe strap slit 164, best seen at FIGS. 1-2 and 4.

As also best seen at FIGS. 1-2 and 4, the toe strap 170 comprises a toe strap first upper end 172, a toe strap second upper end 174, a toe strap first upper flap 176, and a toe strap second upper flap 178. As best seen at FIGS. 1, and 3-4, the toe strap 170 further comprises a toe strap intermediate portion 180. Referring to FIG. 5, the toe strap 170 further comprises a toe strap first lower end 182, a toe strap second lower end 184, a toe strap first lower flap 186, and a toe strap second lower flap 188.

Referring again to FIGS. 1-2, the foot support 100 may comprise an arch support 192 fixed to the mid-foot support 190, the arch support 192 located proximal to the medial side 110 of the foot support 100. The foot support 100 may further comprise a ball of foot pad 194 fixed to the mid-foot support 190 proximal to a central area 196 of the mid-foot support.

As seen at FIG. 5, the upper transverse strap 150 is attached to the sole 120 by fixation of the upper transverse strap medial end distal flap 158 to the sole bottom surface 124 at the medial sole area 128, and fixation of the upper transverse strap lateral end distal flap 162 to the sole bottom surface 124 at the lateral sole area 112. The toe strap intermediate portion 180 extends vertically between the sole 120 and the upper transverse strap 150 (best seen with reference to FIGS. 1 and 3).

With continued reference to FIG. 5, the toe strap first lower flap 186 and the toe strap second lower flap 188 extend downwardly through the lower toe strap slit 126. The toe strap first lower flap 186 is attached to the sole 120 by fixation of the toe strap first lower flap 186 to the sole bottom surface 124. The toe strap second lower flap 188 is attached to the sole 120 by fixation of the toe strap second lower flap 188 to the sole bottom surface 124.

Referring again to FIGS. 1-4, the toe strap first upper flap 176 and the second toe strap upper flap 178 extend upwardly through the upper toe strap slit 164, the toe strap first upper flap 176 is attached to the upper transverse strap 150 by fixation of the toe strap first upper flap 176 to the upper transverse strap top surface 152 and the toe strap second upper flap 178 is attached to the upper transverse strap 150 by fixation of the toe strap second upper flap 178 to the upper transverse strap top surface 152.

The wearer may easily don the foot support 100 by slipping the foot of the wearer 140 into the foot support 100, and may easily remove the foot support 100 by slipping the foot of the wearer 140 out of the foot support 100.

The foot support and its components may be any suitable size and dimensions. The foot support may be provided in a wide range of sizes to fit any foot. It can be seen that the components of the foot support may be relatively thin. Nonlimiting examples of thicknesses may be between 1.0-5.0 mm. The foot support and its components may be made of any suitable materials. In some embodiments the materials may be flexible and resilient, including but not limited to, plastic or foam materials, synthetic materials or natural materials such as fabrics or leather. In some embodiments, the foot support and its components may be made of waterproof materials or include a waterproof coating. The foot support and its components may be made by any suitable fabrication process, including but not limited to 3-D printing, additive manufacturing, injection molding, lamination, adhesive bonding, sewing or mechanical attachment.

In some embodiments, the foot support may further comprise an inner sole affixed to the sole top surface 122.

In some embodiments, the foot support 100 may further comprise an outer sole affixed to the sole bottom surface 124.

The foot support 100 may further comprise an anti-slip bottom. In some embodiments, the sole bottom surface 124 may comprise an integral anti-slip surface. In other embodiments, an outer sole comprising an anti-slip bottom may be affixed to the sole bottom surface 124. The anti-slip surface may comprise any suitable configuration or material, such as, for example without limitation, an anti-slip treatment of the surface to improve anti-slip properties, a high-friction coating, or treads. The foot support 100 with an anti-slip bottom may be worn in the shower so the wearer has continued support and improved stability while standing in the shower.

In summary, the present invention provides a slip-on orthotic foot support constructed and arranged to support the arch and the ball of a wearer's foot. The foot support may be configured as a partial sandal having neither under-toe nor under-heel portions, and comprises a sole defining a mid-foot support affixed to an upper transverse strap, and a retention wedge or toe strap affixed to and extending vertically between the sole and the upper transverse strap. The foot support may additionally include an arch support and a ball-of-foot pad on an upper surface of the sole. The foot support provides hands-free, slip-on and slip-off orthotic "stand-alone" footwear that is not meant to be worn with shoes. The foot support may be beneficially used by the wearer to wear instead of shoes or going barefoot around the house. The foot support may be made of waterproof materials and may include an anti-slip bottom.

The foot support of the present invention distinguishes over and differs from previous solutions. The present invention provides an unprecedented solution in the first hands-free slip-on and slip-off orthotic designed to support the bottom of the mid-foot, and that supports the middle of the foot between the distal end of the heel and the distal end of the metatarsal bones. The foot support provides an arch support and a ball of foot pad, but includes no support or padding under the heel or toes. The foot support is not meant to be worn with shoes. The foot support "end-less sandal" is designed to wear at home, around the wearer's house, condo or apartment, instead of wearing shoes or conventional sandals. Since there is no padding or sole under the heel and toes, walking outside could be uncomfortable depending on the terrain. Wearing the foot support permits wearers to feel like they are walking around barefoot while still having support under the middle soft spot of the foot. The foot support may be beneficially worn by individuals experiencing fallen arches, thinning of the ball of the foot, or many other foot problems.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A slip-on orthotic foot support for supporting a foot arch and a ball of a foot of a wearer as a stand-alone footwear without the wearer having to wear a shoe, the slip-on orthotic foot support having a top, a bottom, a front, a rear, a medial side, and a lateral side, the slip-on orthotic foot support comprising:

a sole having a medial sole area corresponding to the medial side of the slip-on orthotic foot support, and a lateral sole area corresponding to the lateral side of the slip-on orthotic foot support;

an upper transverse strap; and a toe strap;

wherein the upper transverse strap is attached to the sole;

wherein the toe strap is attached to the sole and the upper transverse strap, and the toe strap extends vertically between the sole and the upper transverse strap, wherein the sole comprises a mid-foot support that is configured to be positioned under a mid-foot area of the foot of the wearer between a distal end of a heel of the foot and a distal end of a plurality of metatarsal bones of the foot of the wearer so as to support a bottom of the mid-foot area at the foot arch and the ball of the foot of the wearer, the mid-foot support having a central area between the medial sole area corresponding to the medial side and the lateral sole area corresponding to the lateral side, wherein when the slip-on orthotic foot support is worn by the wearer, the mid-foot support constitutes the only portion of the sole positioned under the foot of the wearer, wherein the slip-on orthotic foot support is free of an under-toe portion for supporting toes of the wearer and an under-heel portion for supporting a heel of the wearer, wherein the slip-on orthotic foot support comprises an arch support fixedly attached to the mid-foot support only at the medial sole area corresponding to the medial side of the slip-on orthotic foot support, wherein the slip-on orthotic foot support comprises a ball of foot pad fixedly attached to the mid-foot support only at the central area of the mid-foot support, and wherein an entirety of the ball of foot pad is positioned closer to the lateral sole area corresponding to the lateral side of the slip-on orthotic foot support as compared to an entirety of the arch support.

2. The slip-on orthotic foot support of claim 1, wherein the sole comprises a sole top surface, a sole bottom surface, and a lower toe strap slit.

3. The slip-on orthotic foot support of claim 2, wherein the upper transverse strap has an upper transverse strap top surface, an upper transverse strap bottom surface, an upper transverse strap medial end, an upper transverse strap medial end distal flap, an upper transverse strap lateral end, an upper transverse strap lateral end distal flap, and an upper toe strap slit.

4. The slip-on orthotic foot support of claim 3, wherein the upper transverse strap is attached to the sole by fixation of the upper transverse strap medial end distal flap to the sole bottom surface at the medial sole area, and fixation of the upper transverse strap lateral end distal flap to the sole bottom surface at the lateral sole area.

5. The slip-on orthotic foot support of claim 4, wherein the toe strap comprises a toe strap first upper end, a toe strap first upper flap, a toe strap second upper end, a toe strap second upper flap, a toe strap intermediate portion, a toe strap first lower end, a toe strap first lower flap, a toe strap second lower end, and a toe strap second lower flap.

6. The slip-on orthotic foot support of claim 5, wherein:

the toe strap intermediate portion extends vertically between the sole and the upper transverse strap;

the toe strap first lower flap and the toe strap second lower flap extend downwardly through the lower toe strap slit; and the toe strap first upper flap and the second toe strap upper flap extend upwardly through the upper toe strap slit.

7. The slip-on orthotic foot support of claim 6, wherein:

the toe strap first lower flap is attached to the sole by fixation of the toe strap first lower flap to the sole bottom surface;

the toe strap second lower flap is attached to the sole by fixation of the toe strap second lower flap to the sole bottom surface;

the toe strap first upper flap is attached to the upper transverse strap by fixation of the toe strap first upper flap to the upper transverse strap top surface; and the toe strap second upper flap is attached to the upper transverse strap by fixation of the toe strap second upper flap to the upper transverse strap top surface.

8. The slip-on orthotic foot support of claim 1 made of waterproof materials.

9. The slip-on orthotic foot support of claim 1 configured to be worn by the user in a shower to provide the wearer continued support while standing in the shower.

10. A slip-on orthotic foot support for supporting a foot arch and a ball of a foot of a wearer as a stand-alone footwear without the wearer having to wear a shoe, the slip-on orthotic foot support having a top, a bottom, a front, a rear, a medial side, and a lateral side, the slip-on orthotic foot support comprising:

a sole comprising a sole top surface, a sole bottom surface, a lower toe strap slit, a medial sole area corresponding to the medial side of the slip-on orthotic foot support and a lateral sole area corresponding to the lateral side of the slip-on orthotic foot support, wherein the sole comprises a mid-foot support that is configured to be positioned under a mid-foot area of the foot of the wearer between a distal end of a heel of the foot and a distal end of a plurality of metatarsal bones of the foot of the wearer so as to support a bottom of the mid-foot area at the foot arch and the ball of the foot of the wearer, the mid-foot support having a central area between the medial sole area corresponding to the medial side and the lateral sole area corresponding to the lateral side;

an upper transverse strap having an upper transverse strap top surface, an upper transverse strap bottom surface, an upper transverse strap medial end, an upper transverse strap medial end distal flap, an upper transverse strap lateral end, an upper transverse strap lateral end distal flap, and an upper toe strap slit;

a toe strap comprising a toe strap first upper end, a toe strap first upper flap, a toe strap second upper end, a toe strap second upper flap, a toe strap intermediate portion, a toe strap first lower end, a toe strap first lower flap, a toe strap second lower end, and a toe strap second lower flap;

an arch support fixedly attached to the mid-foot support only at the medial sole area corresponding to the medial side of the slip-on orthotic foot support; and a ball of foot pad fixedly attached to the mid-foot support only at the central area of the mid-foot support;

wherein an entirety of the ball of foot pad is positioned closer to the lateral sole area corresponding to the lateral side of the slip-on orthotic foot support as compared to an entirety of the arch support;

wherein the upper transverse strap is attached to the sole by fixation of the upper transverse strap medial end distal flap to the sole bottom surface at the medial sole area, and fixation of the upper transverse strap lateral end distal flap to the sole bottom surface at the lateral sole area; and wherein the toe strap intermediate portion extends vertically between the sole and the upper transverse strap, the toe strap first lower flap and the toe strap second lower flap extend downwardly through the lower toe strap slit, the toe strap first lower flap is attached to the sole by fixation of the toe strap first lower flap to the sole bottom surface, the toe strap second lower flap is attached to the sole by fixation of the toe strap second lower flap to the sole bottom surface, the toe strap first upper flap and the second toe strap upper flap extend through the upper toe strap slit, the toe strap first upper flap is attached to the upper transverse strap by fixation of the toe strap first upper flap to the upper transverse strap top surface and the toe strap second upper flap is attached to the upper transverse strap by fixation of the toe strap second upper flap to the upper transverse strap top surface;

wherein the slip-on orthotic foot support is configured to be donned by slipping the foot of the wearer into the slip-on orthotic foot support to support the foot arch and the ball of the foot of the wearer by the slip-on orthotic foot support as a stand-alone footwear without the wearer having to wear a shoe, and the slip-on orthotic foot support is configured to be removed by slipping the foot of the wearer out of the slip-on orthotic foot support, wherein when the slip-on orthotic foot support is worn by the wearer, the mid-foot support constitutes the only portion of the sole positioned under the foot of the wearer, wherein the slip-on orthotic foot support is free of an under-toe portion for supporting toes of the wearer and an under-heel portion for supporting a heel of the wearer.

* * * * *